United States Patent
Koyama et al.

(10) Patent No.: US 6,670,489 B2
(45) Date of Patent: Dec. 30, 2003

(54) PROCESS FOR PRODUCING CYCLIC FORMAL

(75) Inventors: Atsushi Koyama, Kurashiki (JP); Rikio Fujiwara, Kurashiki (JP); Hiroshi Nakatsui, Sodegaura (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/221,487

(22) PCT Filed: Jan. 15, 2002

(86) PCT No.: PCT/JP02/00183

§ 371 (c)(1),
(2), (4) Date: Sep. 13, 2002

(87) PCT Pub. No.: WO02/055513

PCT Pub. Date: Jul. 18, 2002

(65) Prior Publication Data

US 2003/0050483 A1 Mar. 13, 2003

(30) Foreign Application Priority Data

Jan. 15, 2001 (JP) ......................................... 2001-006153

(51) Int. Cl.$^7$ ............................................. C07D 317/12
(52) U.S. Cl. ...................................................... 549/430
(58) Field of Search ...................................... 549/430

(56) References Cited

FOREIGN PATENT DOCUMENTS

| EP | 0 867 434 A1 | 9/1998 |
|---|---|---|
| JP | 53-34670 | 3/1978 |
| JP | 5-155878 A | 6/1993 |
| JP | 5-271217 A | 10/1993 |
| JP | 7-224055 A | 8/1995 |

*Primary Examiner*—Taofiq A. Solola
(74) *Attorney, Agent, or Firm*—Birch, Stewart, Kolasch & Birch, LLP

(57) ABSTRACT

In producing a cyclic formal by feeding an alkylene glycol and a formaldehyde derivative as starting materials to a reaction vessel and reacting them in the presence of a catalyst, the value of amount of alkylene glycol (mole)/ amount of formaldehyde derivative in terms of formaldehyde (mole) is kept at 0.02–0.95 at the time of feeding of the starting materials and at 1.05–50 at the time of reaction of the starting materials. According to this process, the amount of by-product impurities at the reaction step can be reduced, and an additional purification step of the cyclic formal is not needed or can be easily performed.

14 Claims, 3 Drawing Sheets

PROCESS FOR PRODUCING CYCLIC FORMAL

This application is the national phase under 35 U.S.C. §371 of PCT International Application No. PCT/JP02/00183 which has an International filing date of Jan. 15, 2002, which designated the United States of America.

TECHNICAL FIELD

The present invention relates to a process for producing a cyclic formal by reacting an alkylene glycol with a formaldehyde derivative, and particularly to a process for producing a cyclic formal wherein the amount of impurities produced as by-products at the reaction step can be reduced.

BACKGROUND ART

As cyclic formals, there are known, for example, 1,3-dioxolane, 1,4-butanediol formal, diethylene glycol formal, 4-methyl-1,3-dioxolane, 1,3-dioxane, 1,3,5-trioxepane, etc. Hitherto, these are produced by a cyclization reaction of a glycol with an aldehyde, or a cyclization reaction of an alkylene oxide with an aldehyde.

The following processes have been proposed as processes for producing 1,3-dioxolane which is a representative cyclic formal.

West German Patent No.1914209 discloses that 1,3-dioxolane containing 7% of water is obtained in a yield of 96.5% by reacting ethylene glycol with formaldehyde in the presence of an acid catalyst.

Russian Patent No.434737 discloses that 1,3-dioxolane of high purity can be obtained by reacting ethylene glycol with trioxane (hydrous) in the presence of an acid catalyst, subjecting the reaction mixture to extraction with benzene, and additionally subjecting the reaction mixture to washing with a sodium hydroxide solution and rectification.

JP-A-49-62469 discloses that 1,3-dioxolane of high purity is obtained by reacting ethylene glycol with paraformaldehyde in the presence of an acid catalyst, and adding cyclohexane to the reaction distillate liquid, followed by subjecting the reaction mixture to rectification.

However, as a result of an investigation conducted by the inventors, it has been found that in the case of producing a cyclic formal using glycol and formaldehyde as starting materials, if they are reacted using a reactor of the evaporating can type and the vapor after the reaction is continuously discharged, the resulting distillate liquid contains impurities produced at the reaction step and unreacted starting materials (particularly, formaldehyde) in considerably large amounts in addition to the cyclic formal.

The cyclic formal has a property of readily causing azeotropy with water, and, furthermore, if the resulting cyclic formal contains by-product impurities, formaldehyde or the like, purification of the cyclic formal which is a step subsequent to the reaction step becomes further troublesome and complicated. For example, when 1,3-dioxolane is produced using ethylene glycol and trioxane as starting materials, in addition to water as a by-product, there are produced, as impurities, formaldehyde, acetaldehyde, methanol, 2-methyl-1,3-dioxolane, formic acid, 1,4-dioxane, 1,3,5-trioxepane, etc., and all of them incorporate into the distillate liquid. Therefore, in order to obtain 1,3-dioxolane of high purity, separation and removal of these low-boiling point components and high-boiling point components are further needed in addition to separation and removal of water.

The prior art discloses processes for synthesis of a cyclic formal from an alkylene glycol and a formaldehyde derivative, but does not disclose carrying out the reaction while controlling the composition of starting materials used for the reaction at the time when feeding them and at the time of their reaction, thereby inhibiting the production of impurities as by-products. Furthermore, the prior art does not describe the inhibition of the production of impurities by avoiding incorporation of methanol or water into the starting formaldehyde derivative. For example, when 1,3-dioxolane is produced as the cyclic formal, if methanol or formaldehyde is present in the formaldehyde derivative as a starting material, they react with each other to form addition products, and therefore it becomes difficult to separate most of the addition products from 1,3-dioxolane by distillation. In addition, 1,3,5-trioxepane is produced in a large amount during the reaction, and, further, formaldehyde also incorporates into the distillate liquid in a large amount, resulting in reduction of the yield of 1,3-dioxolane.

An object of the present invention is to provide a process for producing a cyclic formal by reacting an alkylene glycol with a formaldehyde derivative, wherein a purification step can be omitted or can be performed easily by reducing the amounts of impurities produced as by-products at the reaction step.

DISCLOSURE OF INVENTION

For attaining the above object, the inventors have conducted an investigation on optimum conditions for reacting an alkylene glycol with a formaldehyde derivative in a reaction vessel. As a result, it has been found that the amounts of impurities produced can be reduced when the molar ratio of the alkylene glycol and the formaldehyde derivative as starting materials is within a specific range at the time of feeding and at the time of reaction of the alkylene glycol and the formaldehyde derivative.

Moreover, it has also been found that the vapor produced under the above reaction conditions entrains by-product impurities, formaldehyde or the like, and incorporation of these impurities, formaldehyde or the like into the produced vapor can be considerably inhibited by supplying the produced vapor to a gas-liquid contacting part to allow the vapor to countercurrently contact with a diluent solution.

It has further been found that 1,3-dioxolane of very high purity can be obtained by separating and removing from the produced vapor the high-boiling point components such as unreacted formaldehyde derivative or formaldehyde produced due to decomposition, and further removing water therefrom.

That is, the present invention relates to the following processes.

[1] A process for producing a cyclic formal which comprises feeding an alkylene glycol and a formaldehyde derivative as starting materials to a reaction vessel and reacting the alkylene glycol and the formaldehyde derivative in the presence of a catalyst in the reaction vessel, characterized in that the value of amount of alkylene glycol (mole)/amount of formaldehyde derivative in terms of formaldehyde (mole) is 0.02–0.95 at the time of feeding of the starting materials and is 1.05–50 at the time of reaction of the starting materials.

[2] A process of the above [1], wherein the formaldehyde derivative is trioxane.

[3] A process of the above [1] which further comprises supplying the vapor produced by the reaction of alkylene glycol and formaldehyde derivative to a gas-liquid contacting part, allowing the vapor to countercurrently contact with a diluent liquid, and drawing the diluent liquid after the countercurrent contact from the gas-liquid contacting part without allowing the diluent liquid to flow into the reaction vessel.

[4] A process of the above [3], wherein the gas-liquid contacting part is an absorption tower.

[5] A process of the above [3], wherein the diluent liquid is pure water.

[6] A process of the above [1] which further comprises separating high-boiling point components, unreacted formaldehyde derivative and formaldehyde produced due to decomposition from the vapor produced by the reaction of alkylene glycol and formaldehyde derivative, and removing water from the vapor obtained after the separation.

[7] A process of the above [6] which further comprises condensing the vapor produced by the reaction of alkylene glycol and formaldehyde derivative, separating high-boiling point components, unreacted formaldehyde derivative and formaldehyde produced due to decomposition from the condensate, and removing water from the liquid obtained after the separation.

[8] A process of the above [6], wherein the removal of water from the liquid obtained after the separation is carried out by contacting the liquid with ethylene glycol in a purification tower, and water is added to the liquid before contacting with ethylene glycol.

[9] A process of the above [8], wherein the vapor in the top part of the purification tower has an oxygen concentration of not more than 1000 vol ppm.

[10] A process of the above [3] which further comprises separating high-boiling point components, unreacted formaldehyde derivative and formaldehyde produced due to decomposition from the vapor after being subjected to the countercurrent contacting and removing water from the liquid obtained after the separation.

[11] A process of the above [10] which further comprises condensing the vapor after being subjected to the countercurrent contacting, separating high-boiling point components, unreacted formaldehyde derivative and formaldehyde produced due to decomposition from the condensate, and removing water from the liquid obtained after the separation.

[12] A process of the above [10], wherein the removal of water from the liquid obtained after the separation is carried out by contacting the liquid with ethylene glycol in a purification tower, and water is added to the liquid before contacting with ethylene glycol.

[13] A process of the above [12], wherein the vapor in the top part of the purification tower has an oxygen concentration of not more than 1000 vol ppm.

[14] A process of any one of the above [1]–[13], wherein the cyclic formal is 1,3-dioxolane.

BEST MODE FOR CARRYING OUT THE INVENTION

Figure 1:
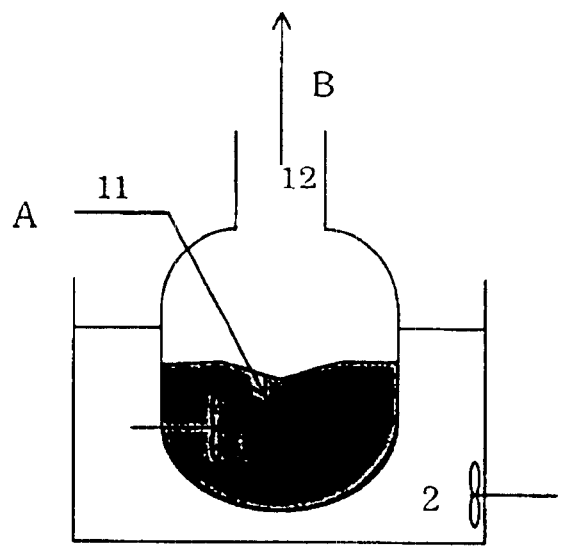
FIG. 1 shows an apparatus for producing cyclic formal which is employed in Examples 1 and 2 and Comparative Examples 1 and 2.

First, starting materials used in the process for producing cyclic formal according to the present invention will be explained.

As the alkylene glycols, those which are represented by the formula $R(OH)_2$ can be used. Here, R is a straight chain or branched chain alkylene group. For example, when 1,3-dioxolane is produced as the cyclic formal, ethylene glycol is used. Similarly, when 1,4-butanediol formal is produced, 1,4-butanediol can be used; when diethylene glycol formal is produced, diethylene glycol can be used; when 4-methyl-1,3-dioxolane is produced, 1,2-propanediol can be used; when 1,3-dioxane is produced, 1,3-propanediol can be used; and when 1,3,6-trioxane is produced, 2-(hydroxymethoxy)ethanol can be used.

As the formaldehyde derivatives, mention may be made of high purity formaldehyde, trioxane, tetraoxane, polyacetal or the like. In the present invention, not only one formaldehyde derivative, but also two or more formaldehyde derivatives may be used as starting material.

It is especially preferred to use high purity trioxane as the formaldehyde derivative. This is because trioxane which is purified to high purity has a melting point at about 64° C. and can be used in the form of a liquid substance upon heating, and, hence, handling such as replenishment or drawing of it can be performed easily and, besides, formaldehyde of high purity can be easily obtained by decomposition with an acid. Trioxane of high purity can be easily obtained by subjecting trioxane to purification as disclosed in, for example, Japanese Patent No.2916953 (pamphlet of International Publication No.96/22986). Since commercially available formalin contains water and methanol, and commercially available paraformaldehyde contains methanol, impurities are apt to be produced during the reaction step.

Next, the catalysts used in the present invention are preferably acidic catalysts. Examples of the catalysts are mineral acids such as sulfuric acid and phosphoric acid, heteropoly-acids, aliphatic or aromatic sulfonic acids such as metasulfonic acid, benzenesulfonic acid, p-toluenesulfonic acid and naphthalenesulfonic acid, and solid acids such as ion-exchange resins, ion-exchange fibers, ion-exchange membranes, zeolite and silica-alumina. The catalysts may be each used alone or in combination of two or more.

As the catalysts, those which are in the form of liquid are preferred because they can be easily drawn or replenished during continuous operation of a production apparatus. Among them, sulfuric acid is especially preferred because it causes decomposition of formaldehyde derivatives such as trioxane at much higher speed than organic acids, and, in addition, it is liquid.

The concentration of the catalysts varies depending on the catalysts selected, and when sulfuric acid is used, the concentration is preferably 0.1–30% by weight, more preferably 1–20% by weight based on the amount of liquid in the reaction vessel at the time of reaction.

The production process of the present invention will be explained.

According to the present invention, the above-mentioned alkylene glycol and formaldehyde are fed to the reaction vessel as starting materials and are reacted in the presence of the above-mentioned catalyst to produce a cyclic formal. The production of the cyclic formal according to the present invention is carried out usually in a continuous manner, but may be carried out in a batch-wise manner.

Specifically, first, alkylene glycol and formaldehyde derivative as starting materials are previously charged in a reaction vessel at a given ratio, and, then, alkylene glycol and formaldehyde derivative are further fed to the reaction vessel and they are reacted in the presence of the above catalyst and under given reaction conditions to produce the desired cyclic formal. Here, the composition of the starting materials in the reaction vessel approaches a certain value during the reaction, and is stabilized at a certain composition. In the present invention, the time when the composition of alkylene glycol and formaldehyde derivative is stabilized and becomes constant during the reaction is defined to be "the time of reaction".

In the present invention, the composition (molar ratio) of alkylene glycol and formaldehyde derivative as starting materials at the time of feeding and the composition (molar ratio) of alkylene glycol and formaldehyde derivative at the time of reaction are important.

Irrespective of the composition of alkylene glycol and formaldehyde derivative at the time of charging, the composition of alkylene glycol and formaldehyde derivative at the time of reaction converges to a certain composition depending on the composition of alkylene glycol and formaldehyde derivative at the time of feeding and the reaction conditions (temperature, pressure, catalyst concentration, etc.).

In the present invention, the amount (mole) of the formaldehyde derivative in terms of formaldehyde must be in excess of the amount (mole) of the alkylene glycol at the time of feeding of the alkylene glycol and the formaldehyde derivative. That is, in the present invention, the value of the amount (mole) of alkylene glycol/the amount (mole) of formaldehyde derivative in terms of formaldehyde must be 0.02–0.95, more preferably 0.05–0.90. By specifying the molar ratio in a specific range, loss of the formaldehyde derivative can be reduced, and the yield of the resulting cyclic formal can be kept at a high level.

On the other hand, at the time of reaction of the starting materials, conversely, the amount (mole) of the alkylene glycol must be in excess of the amount (mole) of the formaldehyde derivative in terms of formaldehyde. That is, in the present invention, the ratio of the amount (mole) of alkylene glycol/the amount (mole) of formaldehyde derivative in terms of formaldehyde must be 1.05–50, more preferably 1.5–20. By specifying the molar ratio in the above specific range, the excess formaldehyde which causes side reaction can be reduced, whereby production of impurities at the reaction step caused by formaldehyde can be inhibited and the yield of the resulting cyclic formal can be maintained. As mentioned above, the value of the amount (mole) of alkylene glycol/the amount (mole) of formaldehyde derivative in terms of formaldehyde at the time of reaction can be in the desired range by adjusting the value of the amount (mole) of alkylene glycol/the amount (mole) of formaldehyde derivative in terms of formaldehyde at the time of feeding and the reaction conditions.

Here, the amount (mole) of formaldehyde derivative in terms of formaldehyde means the amount (mole) which is the total of the amount (mole) of the formaldehyde derivative present at the time of feeding (reaction) of the starting materials which is calculated in terms of formaldehyde (for example, when trioxane is used as the formaldehyde derivative, one mole of trioxane is regarded to be "3 moles" in terms of formaldehyde) and the amount (mole) of formaldehyde produced due to the decomposition of the formaldehyde derivative with acid.

By specifying in a specific range the molar ratio of alkylene glycol and formaldehyde derivative at the time of feeding and at the time of reaction, production of impurities at the reaction step can be inhibited. Taking the case of producing 1,3-dioxolane by the production process of the present invention, it becomes possible to highly inhibit the production of impurities such as acetaldehyde, methanol, 2-methyl-1,3-dioxolane, formic acid, 1,4-dioxane and 1,3,5-trioxepane.

The temperature condition in reacting alkylene glycol with formaldehyde derivative in the presence of catalyst varies depending on the starting materials and the catalyst used, but must be in the range of temperature in which the reaction for production of cyclic formal can proceed and the desired yield of cyclic formal can be maintained. Furthermore, within such temperature range, it is preferred to carry out the reaction at the lower temperature to diminish the production of impurities. Taking the case of producing 1,3-dioxolane, the reaction temperature is preferably 70–150° C., more preferably 90–120° C. in order to inhibit production of impurities such as acetaldehyde and 2-methyl-1,3-dioxolane.

Moreover, the pressure in the reaction vessel is preferably such that most of the cyclic formal and water can evaporate at the above reaction temperature under the pressure, and may be either atmospheric pressure or reduced pressure.

Furthermore, average retention time is preferably 10–500 minutes, more preferably 20–200 minutes. The average retention time is defined as follows.

Average retention time (hr)=Amount of liquid in reaction vessel (L)/Amount of liquid fed (L/hr)

The apparatus used for carrying out the present invention has no limitation, and mention may be made of, for example, the reaction apparatus as shown in FIG. 1 which comprises a reaction vessel 1 and a heating oil bath 2. A specific process for producing a cyclic formal using the apparatus shown in FIG. 1 will be explained below.

Alkylene glycol and formaldehyde derivative are charged in the reaction vessel 1 at a given molar ratio, and catalyst and other ingredients are further added. If the desired cyclic formal is previously charged in the reaction vessel in addition to the alkylene glycol and the formaldehyde derivative, the time required for the composition of the alkylene glycol and the formaldehyde derivative during the reaction to be stabilized and become constant can be shortened. Then, the reaction vessel 1 is heated by the oil bath 2 having a stirring function. The heating of the reaction vessel 1 may be carried out by a jacket method, reboiler or the like.

Next, alkylene glycol and formaldehyde derivative are fed at the above-mentioned specific molar ratio to the reaction vessel 1 through a feeding line 11 provided at the reaction vessel 1. FIG. 1 shows an example of feeding the alkylene glycol and the formaldehyde derivative as a mixed liquid A, but the respective components may be separately fed from separate feeding lines, respectively. Moreover, if necessary, the reaction vessel 1 may be provided with a line for drawing inner liquid of the reaction vessel 1 and a line for additional charging of catalyst. The reaction vessel 1 preferably has a stirring function.

Vapor B produced by the reaction of alkylene glycol with formaldehyde derivative under the above conditions is taken out from a vapor outlet 12 to obtain a cyclic formal which has a lesser content of by-product impurities.

Thus, according to the production process of the present invention, the amount of by-product impurities produced at the reaction step can be reduced, but the vapor produced by the reaction of alkylene glycol with formaldehyde derivative entrains by-product impurities, formaldehyde, etc. in addition to the desired cyclic formal. Furthermore, in case a liquid acidic catalyst is used for the reaction of alkylene glycol with formaldehyde derivative, the entrained acid may incorporate into the produced vapor. Since alkylene glycol readily reacts with acid, if the acid incorporates into the vapor, there are, as impurities, products formed by the addition of alkyl group to the cyclic formal, dimers of alkylene glycol, and the like.

Therefore, in the present invention, it is preferred to supply the vapor to a gas-liquid contacting part, thereby to subject the vapor to countercurrent contact with a diluent liquid. By providing the gas-liquid contacting part, it becomes possible to inhibit incorporation of by-product impurities, formaldehyde and the like into the produced vapor containing the cyclic formal. Taking the case of producing 1,3-dioxolane, it is possible to highly inhibit the incorporation of by-product impurities such as formic acid, 1,4-dioxane and 1,3,5-trioxepane, and formaldehyde, etc.

Furthermore, particularly when a high-boiling point liquid acidic catalyst is used as a catalyst, incorporation of acid into the produced vapor can be diminished by providing a gas-liquid contacting part, and thus economical efficiency of the apparatus at the subsequent purification step can be improved.

Figure 2:
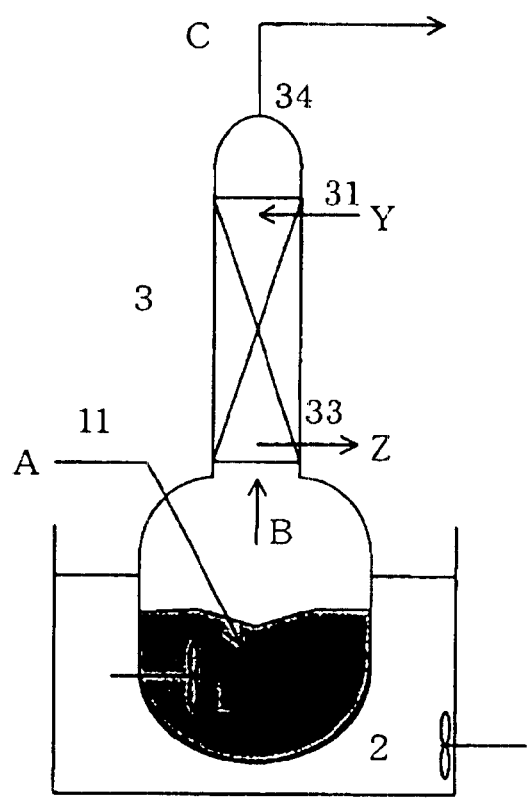
FIG. 2 shows an apparatus for producing cyclic formal which is employed in Examples 3 and 4.

FIG. 2 shows one example of a reaction apparatus provided with a gas-liquid contacting part 3 at the outlet 12 (FIG. 1) of the reaction vessel 1. The gas-liquid contacting part 3 may be provided as an independent tower separately from the reaction vessel 1.

The vapor B produced in the reaction vessel 1 together with entrained by-product impurities and formaldehyde countercurrently contact with a diluent liquid Y supplied from the upper portion of the gas-liquid contacting part 3. Thus, absorption and dilution of the by-product impurities, formaldehyde and the like are performed, whereby it becomes possible to reduce concentrations of these materials present in the vapor B produced in the reaction vessel 1.

The diluent liquid Y is supplied from the uppermost plate 31 of the gas-liquid contacting part 3. The amount of the diluent liquid Y supplied is preferably 1–100% by weight, more preferably 2–50% by weight based on the mass of vapor C drawn from the tower top 34 after the countercurrent contact.

The diluent liquid Y has no particular limitations, and can be any of those which have a higher boiling point than that of cyclic formal to be produced and do not greatly affect the later steps even when they are splashed and incorporated into cyclic formal, such as purified cyclic formal, alkylene glycol, and the like.

In the present invention, pure water is preferred as the diluent liquid Y. This is because it is economically advantageous and, furthermore, high in absorption of formaldehyde which greatly affects the production of impurities. Furthermore, pure water is preferably deaerated pure water decreased in the amount of oxygen dissolved therein.

Temperature of the diluent liquid Y is preferably 5–45° C., more preferably 10–35° C.

Diluent liquid Z containing impurities and the like upon gas-liquid contacting flows downwardly from the upper portion to the lower portion of the gas-liquid contacting part 3, and it is necessary to discharge the diluent liquid Z from the lowermost plate 33 of the gas-liquid contacting part 3 without causing introduction into the reaction vessel 1. Since the diluent liquid Z containing by-product impurities and the like is discharged without flowing into the reaction vessel 1, it becomes possible to inhibit incorporation of the impurities and the like into the reaction vessel 1 and the concentration of the impurities.

In order to perform efficiently the reduction of by-product impurities and the like in the gas-liquid contacting part 3, preferably an absorption tower is used as the gas-liquid contacting part 3, and more preferably a plate absorption tower is used. For example, there can be employed all types such as a valve cap tray, Uniflux tray, valve tray, Natta valve tray, ballast tray, sieve tray, and ventri tray. When an Oldershaw tower is used, the number of plates of the absorption tower is 1 or more, preferably 3 or more. On the other hand, with an increase in the number of plates, the plant cost increases to cause a decrease in economical efficiency, and, hence, when an Oldershaw tower is used, the number of plates is 20 or less, preferably 15 or less.

Figure 3:
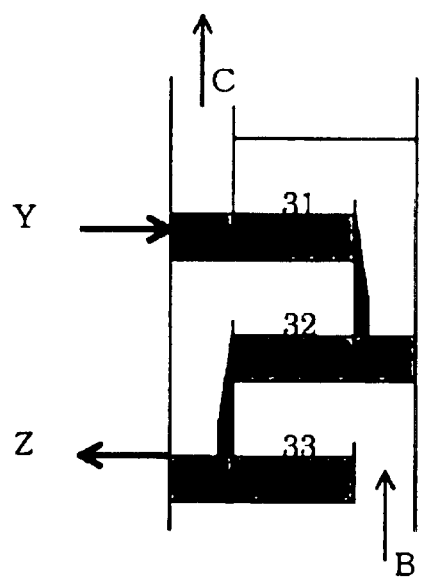
FIG. 3 shows the state of countercurrent contact in the case of using a plate type absorption tower which is one example of the gas-liquid contacting part in the present invention.
Figure 4:
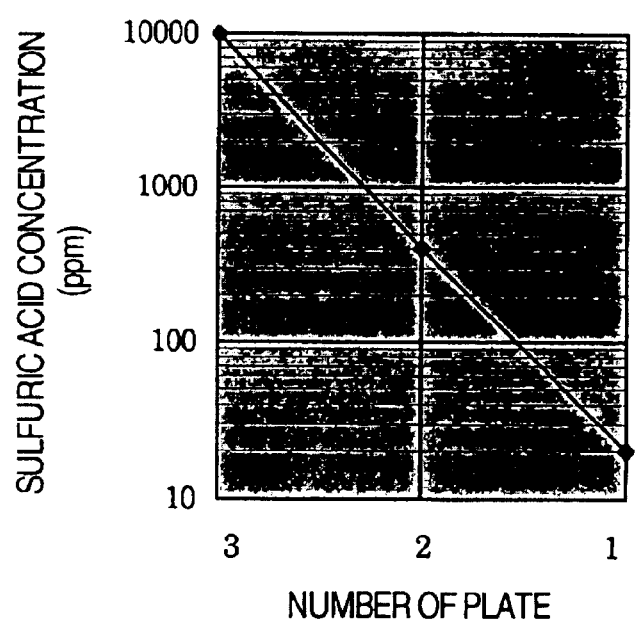
FIG. 4 is a graph which shows change of sulfuric acid concentration at each plate when the countercurrent contact is carried out in the absorption tower shown in FIG. 3.

FIG. 3 shows one example of countercurrent contact using a plate absorption tower. FIG. 4 shows changes of sulfuric acid concentration at the respective plates when the vapor produced in the case of carrying out the reaction of alkylene glycol with formaldehyde derivative using sulfuric acid (catalyst) is countercurrently contacted with a diluent liquid in the absorption tower shown in FIG. 3.

The absorption tower shown in FIG. 3 is a plate tower having a tower diameter of 500 mmφ and a number of plates of 3. The vapor B is a vapor produced by the reaction of alkylene glycol and formaldehyde derivative in the reaction vessel 1, and the diluent liquid Y supplied at the uppermost plate 31 is pure water. The vapor B countercurrently contacts with the diluent liquid Y supplied at the respective plates and is drawn from tower top 34 (FIG. 2) as vapor C. The diluent liquid Z containing by-product impurities, formaldehyde, alkylene glycol and the like after contacting with vapor B is drawn from the lowermost plate 33 which is the third plate.

In this case, concentration of sulfuric acid at the respective plates is 10000 ppm (1%) at the third plate (the lowermost plate 33), which lowers to 20 ppm at the first plate (the uppermost plate 31), as shown in FIG. 4. FIG. 4 shows the change at the respective plates of the sulfuric acid concentration as a representative of high-boiling point impurities, and similarly the concentration lowers also for other high-boiling point impurities.

According to the process for producing cyclic formal of the present invention explained above, the amount of the by-product impurities and formaldehyde contained can be markedly reduced. Therefore, there can be obtained cyclic formal which is directly usable for various uses without further purification. Even in the case of further purifying the resulting cyclic formal to prepare cyclic formal very low in the content of by-product impurities, the purification step of cyclic formal can be performed more easily by using the production process of the present invention.

At the purification step, water can be separated from the resulting cyclic formal, and, further, concentration of the by-product impurities, formaldehyde or the like can be lowered. Taking the case of producing 1,3-dioxolane, concentration of impurities such as acetaldehyde, formic acid, 1,4-dioxane and 1,3,5-trioxepane, and trioxane, formaldehyde or the like can be sharply lowered.

At this purification step, the vapor (vapor B in FIG. 1) produced by the reaction of alkylene glycol and formaldehyde derivative can be directly introduced, or it may be the vapor (vapor C in FIG. 2) obtained after the vapor B is subjected to the countercurrent contacting. Furthermore, the vapor may be condensed by a condenser and introduced as a condensate. That is, at the purification step, high-boiling point components such as unreacted formaldehyde derivative or formaldehyde produced upon decomposition are separated and removed from the vapor or the condensate, and furthermore water is also removed, resulting in 1,3-dioxolane of high purity.

The method of further purification of the resulting cyclic formal has no limitations, and any methods can be employed as long as they can separate and remove the by-product impurities to the desired extent. In general, distillation, azeotropic distillation, extraction distillation, salting-out, etc. can be employed.

Figure 5:
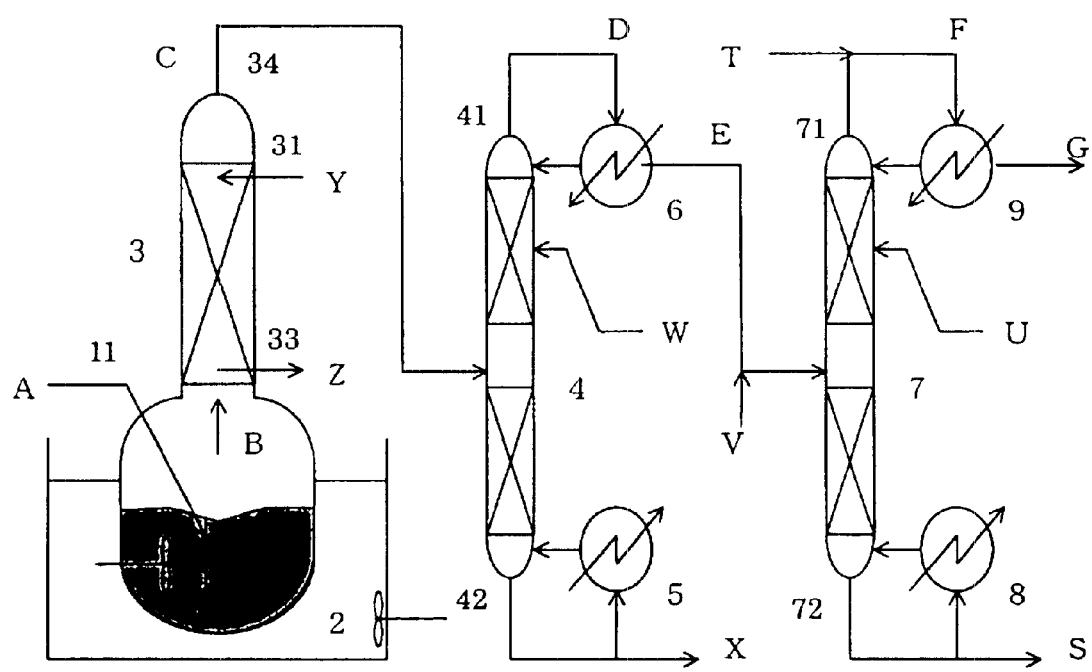
FIG. 5 shows an apparatus for producing cyclic formal which is employed in Examples 5 and 6.

An example of a preferred purification step will be explained referring to FIG. 5. FIG. 5 shows a distillation equipment as a purification apparatus, and the purification apparatus comprises a separation recovery tower 4 and an extraction purification tower 7. In FIG. 5, vapor C drawn from tower top 34 of gas-liquid contacting part 3 is supplied to the separation recovery tower 4 as it is, but as mentioned above, the vapor C may be condensed by a condenser and may be sent to the separation recovery tower 4 as a liquid (condensate).

The type of the separation recovery tower 4 has no limitations, and there may be employed those of all types as long as they are widely industrially employed plate towers. For example, there may be employed a valve cap tray, Uniflux tray, valve tray, Natta valve tray, ballast tray, sieve tray, ventri tray, etc. In the case of using an Oldershaw tower, the number of plates of the separation recovery tower 4 is 20 or more, preferably 30 or more. Moreover, the separation recovery tower 4 may be a packed tower, and as for the packing, there may also be used all types such as a ring type, saddle type, Dickson ring, MacMahon packing, spray pack, etc.

The vapor C after the gas-liquid contacting is contacted with pure water W in the separation recovery tower 4, whereby high-boiling point components, unreacted formaldehyde derivative and formaldehyde produced upon decomposition can be absorbed and separated. The separated formaldehyde derivative and formaldehyde may be recovered from tower bottom 42 and purified, and reused.

The position at which pure water is supplied in the separation recovery tower 4 is preferably in the upper portion which is a middle plate or higher of the separation recovery tower 4 and/or in the refluxing line which connects the condenser 6 and the separation recovery tower 4, and this position is efficient. Moreover, the position at which vapor C is supplied is preferably at a lower plate than the position of supply of pure water W for enhancing the separation efficiency of formaldehyde, and furthermore the vapor C can be supplied at each of the plates below the position of supply of pure water W.

The amount of pure water W supplied here is preferably 50–500% by weight, more preferably 100–300% by weight based on the mass of the resulting purified cyclic formal G.

In the separation recovery tower 4, heating of a mixed liquid (bottom) X of water, formaldehyde and the like drawn from the bottom 42 is carried out by reboiler 5, and it is preferred to carry out the operation so that the temperature at the bottom portion is near the boiling point of the can effluent X under the pressure at the heating, and the temperature at the top portion is near the boiling point of the cyclic formal under the pressure at the heating. The heating method may be an oil bath method, jacket method, and others.

Vapor D after separation from the tower top 41 is cooled by condenser 6, and a part of the resulting condensate E is returned to the separation recovery tower 4 through the refluxing line, and the remainder is supplied to an extraction purification tower 7. Here, the reflux ratio represented by (amount of condensate refluxed to separation recovery tower)/(amount of resulting cyclic formal) is preferably in the range of 0.1–10, more preferably in the range of 0.5–5.

Water can be separated from the condensate E to a high degree by allowing the condensate E separated from the separation recovery tower 4 to countercurrently contact with ethylene glycol U in the extraction purification tower 7.

The type of the extraction purification tower 7 also has no limitations, and any types of plate towers industrially widely employed can be employed. For example, there may be employed a valve cap tray, Uniflux tray, valve tray, Natta valve tray, ballast tray, sieve tray, ventri tray, etc. In the case of using an Oldershaw tower, the number of the plates of the extraction purification tower 7 is 30 or more, preferably 40 or more. Moreover, the extraction purification tower 7 may be a packed tower, and as for the packing, there may also be used all types such as a ring type, saddle type, Dickson ring, MacMahon packing, spray pack, etc.

It is preferred that at the time of supply of the condensate E to the extraction purification tower 7, pure water V is added thereto and mixed therewith to lower the temperature of the condensate E supplied to the extraction purification tower 7. The amount of the pure water V supplied is preferably 2–100% by weight, more preferably 5–50% by weight based on the mass of the resulting purified cyclic formal G. Thus, the number of plates of the extraction purification tower 7 can be reduced, and this is economically effective.

The position at which ethylene glycol U is supplied in the extraction purification tower 7 is preferably in the upper portion of a middle plate or higher of the extraction purification tower 7, and this is efficient and preferred. Moreover, the position at which the condensate E from the separation recovery tower 4 is supplied may be any plate below the middle plate or the bottom of the extraction purification tower 7, but supply of the condensate E at a lower position can result in cyclic formal of higher purity.

The amount of ethylene glycol U supplied here is preferably 100–2000% by weight, more preferably 200–1000% by weight based on the mass of the resulting purified cyclic formal G.

Water and ethylene glycol containing high-boiling point impurities are drawn from bottom 72 together with ethylene glycol U supplied to the extraction purification tower 7.

In the extraction purification tower 7, heating of a mixed liquid (can effluent) S of ethylene glycol, water and the like is carried out by reboiler 8, and it is preferred to carry out the operation so that the temperature of the bottom portion is near the boiling point of the can effluent S under the pressure at the heating, and the temperature of the top portion is near the boiling point of the cyclic formal under the pressure at the heating. The heating method may be an oil bath method, jacket method, and others.

Vapor F is drawn from the tower top 71 of the extraction purification tower 71, and a part of the vapor is cooled by condenser 9, and a part of the resulting condensate G is returned to the extraction purification tower 7, and the remainder is obtained as a purified cyclic formal. The reflux ratio is preferably in the range of 0.2–15, more preferably in the range of 1–10.

Concentration of oxygen in the vapor F in the top portion of the extraction purification tower 7 is preferably not more than 1000 vol ppm, and more preferably is maintained at not more than 800 vol ppm. In the range of the above oxygen concentration, the amount of peroxides produced and contained in the purified cyclic formal can be conspicuously reduced. The means for keeping the oxygen concentration of the vapor F in the above preferred range has no particular limitations, and mention may be made of, for example, a method of introducing inert gas, a method of passing the vapor through a packed tower containing an antioxidant, and the like.

EXAMPLE

The present invention will be explained in more detail, taking the case of producing 1,3-dioxolane as the cyclic formal. This should not be construed as limiting the invention in any manner. First, a method of measuring the composition of the vapor produced will be shown below.
(Analysis of Composition of Product)

A gas chromatograph manufactured by Shimadzu Seisakusho, Ltd. was used for the analysis of composition of the vapor produced. Quantitative determination of each component was conducted by an absolute calibration method. Details of the gas chromatograph used for the analysis are shown in Table 1. Quantitative determination of formic acid was conducted by titration.

TABLE 1

| Composition of analysis | Analytical method | Type | Detection | Column |
| --- | --- | --- | --- | --- |
| 1,3-Dioxolane | Gas chromatograph | GC-14A | TCD | Porapak T |
| Ethylene glycol | Gas chromatograph | GC-14A | TCD | Porapak T |
| 1,3,5-Trioxepane | Gas chromatograph | GC-8A | FID | Thermon 1000 |
| Trioxane | Gas chromatograph | GC-14A | TCD | Porapak T |
| 1,4-Dioxane | Gas chromatograph | GC-8A | FID | Thermon 1000 |
| Water | Gas chromatograph | GC-14A | TCD | Porapak T |
| Formic acid | Titration: BTB solution with 1/100 N KOH was used as an indicator (end point: yellow → green) | | | |
| 2-Methyl-1,3-dioxolane | Gas chromatograph | GC-8A | FID | Porapak T |
| Methanol | Gas chromatograph | GC-14A | FID | Poraplot Q |
| Acetaldehyde | Gas chromatograph | GC-14A | FID | Poraplot Q |
| Formaldehyde | Gas chromatograph | GC-14A | TCD | Porapak T |

*Gas chromatographs used were manufactured by Shimadzu Seisakusho Ltd.

Example 1

The apparatus shown in FIG. 1 was used. Thirty-five grams of ethylene glycol, 1.7 g of trioxane (amount of ethylene glycol (mole)/amount of trioxane in terms of formaldehyde (mole)=11.3), 8.3 g of 1,3-dioxolane, 45 g of pure water and 10 g of sulfuric acid were charged in a reaction vessel 1 of 300 ml, and were heated by an oil bath 2 so as to keep them at 105–115° C. The pressure in the reaction vessel 1 was atmospheric pressure.

Then, a mixed liquid of ethylene glycol and trioxane (amount of ethylene glycol (mole)/amount of trioxane in terms of formaldehyde (mole)=0.65–0.75) was continuously fed to the reaction vessel 1. The mixed liquid was fed so that the liquid level in the reaction vessel 1 was kept constant.

The retention time was 1 hour, and the composition of inner liquid in the reaction vessel 1, composition of the distillate vapor, amount of the distillate vapor, etc. did not greatly change from those at the start of the reaction and were stable (amount of ethylene glycol (mole)/amount of trioxane in terms of formaldehyde (mole)=11.0–12.0). After a lapse of 10 hours from the starting of the reaction, the produced vapor B was condensed, and the composition of the condensate was analyzed. The results are shown in Table 2. According to the process of the present invention, 1,3-dioxolane low in contents of by-product impurities, formaldehyde and the like could be obtained.

Example 2

The apparatus shown in FIG. 1 was used as in Example 1. Thirty-five grams of ethylene glycol, 5 g of trioxane (amount of ethylene glycol (mole)/amount of trioxane in terms of formaldehyde (mole)=3.4), 30 g of 1,3-dioxolane, 20 g of pure water and 10 g of sulfuric acid were charged in the reaction vessel 1 of 300 ml, and were heated by the oil bath 2 so that they were kept at 95–105° C. The pressure in the reaction vessel 1 was 67 kPa.

Then, a mixed liquid of ethylene glycol and trioxane (amount of ethylene glycol (mole)/amount of trioxane in terms of formaldehyde (mole)=0.75–0.85) was continuously fed to the reaction vessel 1. The mixed liquid was fed so that the liquid level in the reaction vessel 1 was kept constant.

The retention time was 1 hour, and the composition of inner liquid in the reaction vessel 1, composition of the distilled vapor, amount of the distilled vapor, etc. did not greatly change from those at the start of the reaction and were stable (amount of ethylene glycol (mole)/amount of trioxane in terms of formaldehyde (mole)=3.0–4.0). After a lapse of 10 hours from the starting of the reaction, the produced vapor B was condensed, and the composition of the condensate was analyzed. The results are shown in Table 2. According to the process of the present invention, 1,3-dioxolane low in contents of by-product impurities, formaldehyde and the like could be obtained.

Example 3

The apparatus shown in FIG. 2 was used. First, in the same manner as in Example 1, the reaction of ethylene glycol and trioxane was carried out in the reaction vessel 1.

Then, the vapor B produced was supplied to the absorption tower 3 (number of plates: 5 plates) and was countercurrently contacted with the purified 1,3-dioxolane supplied from the uppermost plate 31 of the absorption tower 3. The vapor C after being subjected to the countercurrent contact was discharged from the top 34 of the absorption tower. The amount of the purified 1,3-dioxolane supplied was about 10% by weight based on the vapor C produced. The purified 1,3-dioxolane after the countercurrent contact was continuously drawn from the lowermost plate of the absorption tower 3.

As in Example 1, after a lapse of 10 hours from the start of the reaction, the resulting vapor C was condensed and the composition of this condensate was analyzed. The results are shown in Table 2. By additionally carrying out the countercurrent contact in the gas-liquid contacting part in the process of Example 1, 1,3-dioxolane which was lower in by-product impurities could be obtained.

Example 4

The reaction of ethylene glycol and trioxane was carried out in the reaction vessel 1 in the same manner as in Example 3, except that pure water was used in place of the purified 1,3-dioxolane used in Example 3, and the countercurrent contact was carried out in the gas-liquid contacting part 3.

As in Example 1, after a lapse of 10 hours from the start of the reaction, the resulting vapor C was condensed and the composition of the condensate was analyzed. The results are shown in Table 2. By additionally carrying out the countercurrent contact in the gas-liquid contacting part in the process of Example 1, 1,3-dioxolane which was lower in contents of by-product impurities could be obtained. Furthermore, since pure water was used as the diluent liquid in Example 4, the amount of by-product impurities contained in 1,3-dioxolane could be further reduced as compared with that in Example 3 where purified 1,3-dioxolane was used as the diluent liquid.

Example 5

The apparatus shown in FIG. 5 was used. The reaction conditions of ethylene glycol and trioxane in the reaction vessel 1 and the countercurrent contacting conditions in the gas-liquid contacting part 3 were the same as in Example 4.

Furthermore, in order to separate unreacted trioxane and formaldehyde from the vapor C after the gas-liquid contacting, the vapor C was countercurrently contacted with pure water W in the separation recovery tower 4 and additionally with ethylene glycol U in the extraction purification tower 7.

An Oldershaw tower (the number of plates: 30 plates in total) was used as the separation recovery tower 4, and the position at which the vapor C was supplied was the 10th plate. The amount of the supplied pure water W was 150 g/h, and the position of supply was the 5th plate from the top. The condensate was returned to the uppermost plate with a reflux ratio of about 2.0.

An Oldershaw tower (the plate number: 40 plates in total) was used as the extraction purification tower 7, and the condensate E from the separation recovery tower 4 was supplied at the 30th plate from the top. The condensate E was mixed with pure water V at 15 g/h in order to lower the liquid temperature. The amount of ethylene glycol U supplied was 750 g/h, and the position of supply was the 25th plate from the top, and the condensate was returned to the uppermost plate with a reflux ratio of 5.

As in Example 1, after a lapse of 10 hours from the start of the reaction, the resulting vapor F was condensed and the composition of the condensate was analyzed. The results are shown in Table 2. By additionally carrying out the countercurrent contact with water in the gas-liquid contacting part and further carrying out the countercurrent contact with pure water in the separation recovery tower and with ethylene glycol in the extraction purification tower in the process of Example 1, 1,3-dioxolane which was very low in contents of by-product impurities could be obtained. That is, it was found that in Example 5, trioxane and formaldehyde were removed by carrying out the countercurrent contact with pure water in the separation recovery tower, and water was removed by carrying out the countercurrent contact with ethylene glycol in the extraction purification tower.

Example 6

The apparatus shown in FIG. 5 was used. The reaction conditions of ethylene glycol and trioxane in the reaction vessel 1, the countercurrent contacting conditions in the gas-liquid contacting part 3, and the countercurrent contacting conditions in the separation recovery tower 4 and the extraction purification tower 7 were the same as in Example 5, except that nitrogen was supplied to the line from the top 71 of the extraction purification tower 7, and the oxygen concentration in the vapor F was not more than 1000 vol ppm. As a result, the concentration of peroxides contained in the resulting 1,3-dioxolane could be reduced to half or less (not more than 1 ppm) of the concentration in Example 5.

Comparative Example 1

The apparatus shown in FIG. 1 was used as in Example 1. Thirty-five grams of ethylene glycol, 1.5 g of trioxane (amount of ethylene glycol (mole)/amount of trioxane in terms of formaldehyde (mole)=11.3), 8.5 g of 1,3-dioxolane, 45 g of pure water and 10 g of sulfuric acid were charged in the reaction vessel 1 of 300 ml, and were heated by the oil bath 2 so that they were kept at 105–115° C. The pressure in the reaction vessel 1 was atmospheric pressure.

Then, a mixed liquid of ethylene glycol and trioxane (amount of ethylene glycol (mole)/amount of trioxane in terms of formaldehyde (mole)=0.9–1.0) was continuously supplied to the reaction vessel 1. This supply was carried out so that the liquid level in the reaction vessel 1 was kept constant.

As in Example 1, after a lapse of 10 hours from the start of the reaction, the resulting vapor B was condensed and the composition of the condensate was analyzed. The results are shown in Table 2. Since in Comparative Example 1, the concentration of ethylene glycol increased at the time of the reaction of the starting materials (amount of ethylene glycol (mole)/amount of trioxane in terms of formaldehyde (mole)=70–150), the boiling point of the reaction mixture rose, and the amount of the distillate vapor decreased, resulting in an increase of retention time. As a result, amounts of by-product impurities and unreacted ethylene glycol increased in Comparative Example 1, and, furthermore, the yield of 1,3-dioxolane decreased.

Comparative Example 2

The apparatus shown in FIG. 1 was used as in Example 1. Thirty-five grams of ethylene glycol, 1.5 g of trioxane (amount of ethylene glycol (mole)/amount of trioxane in terms of formaldehyde (mole)=11.3), 8.5 g of 1,3-dioxolane, 45 g of pure water and 10 g of sulfuric acid were charged in the reaction vessel 1 of 300 ml, and were heated by the oil bath 2 so that they were kept at 105–115° C. The pressure in the reaction vessel 1 was atmospheric pressure.

Then, a mixed liquid of ethylene glycol and trioxane (amount of ethylene glycol (mole)/amount of trioxane in terms of formaldehyde (mole)=0.3–0.4) was continuously supplied to the reaction vessel 1. This supply was carried out so that the liquid level in the reaction vessel 1 was kept constant.

As in Example 1, after a lapse of 10 hours from the start of the reaction, the resulting vapor B was condensed and the composition of the condensate was analyzed. The results are shown in Table 2. In Comparative Example 2, the concentration of trioxane increased at the time of the reaction of the starting materials (amount of ethylene glycol (mole)/amount of trioxane in terms of formaldehyde (mole)=0.5–1.0), and, therefore, the boiling point of the reaction mixture was lowered, and the amount of the distillate vapor increased. However, in Comparative Example 2, the conversion of supplied trioxane decreased, and, hence, the amount of unreacted trioxane increased and the yield decreased.

TABLE 2

| | Example 1 | Example 2 | Example 3 | Example 4 | Example 5 | Comparative Example 1 | Comparative Example 2 |
|---|---|---|---|---|---|---|---|
| Sample for analysis of composition | Vapor B | Vapor B | Vapor C | Vapor C | Vapor F | Vapor B | Vapor B |
| Construction of apparatus  Reaction vessel | Used | Used | Used | Used | Used | Used | Used |
| Gas-liquid contacting part (Diluent liquid) | Not used | Not used | Used (1,3-dioxalane) | Used (Pure water) | Used (Pure water) | Not used | Not used |
| Separation recovery tower Extraction purification tower | Not used | Not used | Not used | Not used | Used | Not used | Not used |
| Production conditions  Temperature (° C.) | 105–115 | 95–105 | 105–115 | 105–115 | 105–115 | 105–115 | 105–115 |
| Pressure | Atmospheric pressure | 67(kPa) | Atmospheric pressure | Atmospheric pressure | Atmospheric pressure | Atmospheric pressure | Atmospheric pressure |
| Molar ratio*  At the time of feeding | 0.65–0.75 | 0.75–0.85 | 0.6–0.7 | 0.6–0.7 | 0.6–0.7 | 0.9–1.0 | 0.3–0.4 |
| At the time of reaction | 11.0–12.0 | 3.0–4.0 | 11.0–12.0 | 11.0–12.0 | 11.0–12.0 | 70–150 | 0.5–1.0 |
| Composition of Condensate (wt %) | | | | | | | |
| 1,3-Dioxolane | 66.0 | 72.3 | 67.8 | 66.2 | 99.9 | 68.9 | 50.1 |
| Ethylene glycol | 1.2 | 0.6 | 0 | 0 | 0 | 6.5 | 0.1 |
| 1,3,5-Trioxepane | 0.230 | 0.17 | 0.015 | 0.010 | 0 | 0.324 | 0.242 |
| Trioxane | 13.9 | 7.7 | 12.8 | 12.7 | 0 | 4.8 | 34.5 |
| 1,4-Dioxane | 0.004 | 0.004 | 0.002 | 0.001 | 0 | 0.052 | 0.005 |
| Water | 17.5 | 18.0 | 17.1 | 20.6 | 0.004 | 16.8 | 12.4 |
| Formic acid | 0.006 | 0.001 | 0.003 | 0.001 | 0 | 0.031 | 0.006 |
| 2-Methyl-1,3-dioxolane | 0.002 | 0.004 | 0.002 | 0.002 | 0.002 | 0.004 | 0.004 |
| Methanol | 0.005 | 0.009 | 0.005 | 0.005 | 0.005 | 0.012 | 0.005 |
| Acetaldehyde | 0.004 | 0.004 | 0.004 | 0.004 | 0.002 | 0.008 | 0.004 |
| Formaldehyde | 1.2 | 1.2 | 0.9 | 0.6 | 0 | 1.2 | 2.8 |

*Molar ratio = (Amount of ethylene glycol (mole))/(Amount of trioxane in terms of formaldehyde (mole))

INDUSTRIAL APPLICABILITY

According to the process of the present invention, the production of by-product impurities during the reaction of alkylene glycol and formaldehyde derivative can be diminished, and, therefore, it becomes possible to obtain cyclic formal with a lower content of by-product impurities. Thus, further purification of the cyclic formal can be omitted or easily performed, and the process of the present invention is highly suitable as a process for producing cyclic formal effective as starting materials for solvents, medical intermediates, acetal resins, etc.

We claim:

1. A process for producing a cyclic formal which comprises feeding an alkylene glycol and a formaldehyde derivative as starting materials to a reaction vessel and reacting the alkylene glycol and the formaldehyde derivative in the presence of a catalyst in the reaction vessel, wherein the value of amount of the alkylene glycol (mole)/amount of the formaldehyde derivative in terms of formaldehyde (mole) is 0.02–0.95 at the time of feeding of the starting materials and is 1.05–50 at the time of reaction of the starting materials.

2. A process according to claim 1, wherein the formaldehyde derivative is trioxane.

3. A process according to claim 1 which further comprises supplying the vapor produced by the reaction of alkylene glycol and formaldehyde derivative to a gas-liquid contacting part, allowing the vapor to countercurrently contact with a diluent liquid, and drawing the diluent liquid after the countercurrent contact from the gas-liquid contacting part without allowing the diluent liquid to flow into the reaction vessel.

4. A process according to claim 3, wherein the gas-liquid contacting part is an absorption tower.

5. A process according to claim 3, wherein the diluent liquid is pure water.

6. A process according to claim 1 which further comprises separating high-boiling point components, unreacted formaldehyde derivative and formaldehyde produced due to decomposition from the vapor produced by the reaction of alkylene glycol and formaldehyde derivative, and removing water from the vapor obtained after the separation.

7. A process according to claim 6 which further comprises condensing the vapor produced by the reaction of alkylene glycol and formaldehyde derivative, separating high-boiling point components, unreacted formaldehyde derivative and formaldehyde produced due to decomposition from the condensate, and removing water from the liquid obtained after the separation.

8. A process according to claim 6, wherein the removal of water from the liquid obtained after the separation is carried out by contacting the liquid with ethylene glycol in a purification tower, and water is added to the liquid before contacting with ethylene glycol.

9. A process according to claim 8, wherein the vapor in the top of the purification tower has an oxygen concentration of not more than 1000 vol ppm.

10. A process according to claim 3 which further comprises separating high-boiling point components, unreacted formaldehyde derivative and formaldehyde produced by decomposition from the vapor after being subjected to the countercurrent contacting and removing water from the vapor obtained after the separation.

11. A process according to claim 10 which further comprises condensing the vapor after being subjected to the countercurrent contacting, separating high-boiling point components, unreacted formaldehyde derivative and formaldehyde produced due to decomposition from the condensate, and removing water from the liquid obtained after the separation.

12. A process according to claim 10, wherein the removal of water from the liquid obtained after the separation is carried out by contacting the liquid with ethylene glycol in a purification tower, and water is added to the liquid before contacting with ethylene glycol.

13. A process according to claim 12, wherein the vapor in the top part of the purification tower has an oxygen concentration of not more than 1000 vol ppm.

14. A process according to any one of claims 1–13, wherein the cyclic formal is 1,3-dioxolane.

* * * * *